(12) United States Patent
Nakazawa

(10) Patent No.: US 8,148,524 B2
(45) Date of Patent: Apr. 3, 2012

(54) PROCESS FOR PRODUCING SULFONYL CHLORIDE COMPOUND

(75) Inventor: Koichi Nakazawa, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 733 days.

(21) Appl. No.: 12/064,868

(22) PCT Filed: Aug. 22, 2006

(86) PCT No.: PCT/JP2006/316813
§ 371 (c)(1), (2), (4) Date: Feb. 26, 2008

(87) PCT Pub. No.: WO2007/026625
PCT Pub. Date: Mar. 8, 2007

(65) Prior Publication Data
US 2009/0247748 A1    Oct. 1, 2009

(30) Foreign Application Priority Data
Aug. 30, 2005 (JP) .................. 2005-248846

(51) Int. Cl.
*C07D 487/04* (2006.01)
*A01N 33/00* (2006.01)

(52) U.S. Cl. ........................ 544/236; 504/186

(58) Field of Classification Search .......... 544/236
See application file for complete search history.

(56) References Cited

U.S. PATENT DOCUMENTS

| | | | |
|---|---|---|---|
| 4,994,571 A | 2/1991 | Miki et al. | |
| 5,017,212 A | 5/1991 | Ishida et al. | |
| 2005/0032650 A1 | 2/2005 | Tanaka et al. | |
| 2005/0171108 A1 | 8/2005 | Tabuchi et al. | |
| 2010/0204235 A1* | 8/2010 | Lizos et al. | 514/248 |

FOREIGN PATENT DOCUMENTS

| | | |
|---|---|---|
| EP | 1 466 527 A1 | 10/2004 |
| JP | 1-316379 A | 12/1989 |
| JP | 01316379 * | 12/1989 |

OTHER PUBLICATIONS

Suter, et al., JACS, 60 (3), 1938, 538-540.*
Sulkowski, et al., Study of sulfonation of expanded polystyrene waste and properties of products obtained, downloaded Oct. 8, 2010, http://www.thefreelibrary.com/Study+of+the+sulfonation+of+expanded+polystyrene+waste+and+of...-a0216339275.*
Buckles, et al., J. Org. Chem., 1960, 25 (1), 20-24.*
Moiseenkov, et al., Russian Chem. Bull., 35 (11), 2400-2402, 1987.*
TW Office Action issued Oct. 12, 2011 in counterpart TW Application No. 095131380.

* cited by examiner

*Primary Examiner* — James O Wilson
*Assistant Examiner* — Cecilia M Jaisle
(74) *Attorney, Agent, or Firm* — Panitch Schwarze Belisario & Nadel LLP

(57) ABSTRACT

A process for producing a sulfonyl chloride compound comprising:
(A) a step comprising reacting a pyridazine compound represented by the formula (1):

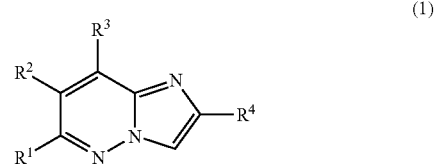

(1)

wherein $R^1$ represents a hydrogen atom, a halogen atom, an alkyl group which may be substituted with a halogen atom or atoms, or the like, $R^2$ and $R^3$ are the same or different and each represents a hydrogen atom or the like, $R^4$ represent a hydrogen atom, a halogen atom, an alkyl group which may be substituted with a halogen atom or atoms, or the like,
with a sulfonating agent;
(B) a step comprising contacting the reaction mixture obtained in the step (A) with a chlorinating agent; and
(C) a step comprising mixing the reaction mixture obtained in the step (B) with an aqueous inorganic base solution to separate an organic layer containing a sulfonyl chloride compound represented by the formula (2):

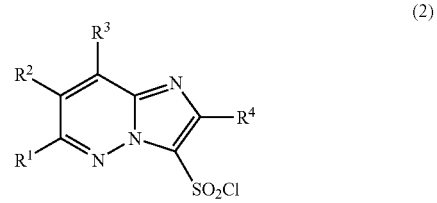

(2)

wherein $R^1$ to $R^4$ are the same meanings as defined above.

11 Claims, No Drawings

PROCESS FOR PRODUCING SULFONYL CHLORIDE COMPOUND

CROSS-REFERENCE TO RELATED APPLICATION

This application is a section 371 of International Application No. PCT/JP2006/316813, filed Aug. 22, 2006, which was published in the Japanese language on Mar. 8, 2007 under International Publication No. WO 2007/026625 A1 and the disclosure of which is incorporated herein by reference.

TECHNICAL FIELD

The present invention relates to a process for producing a sulfonyl chloride compound.

BACKGROUND ART

It has been known that a sulfonyl chloride compound represented by the formula (2):

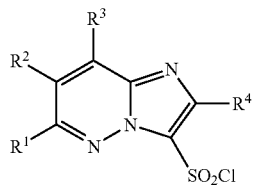

(2)

wherein $R^1$ represents a hydrogen atom, a halogen atom, an alkyl group which may be substituted with a halogen atom or atoms, an alkenyl group which may be substituted with a halogen atom or atoms, an alkynyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, $R^2$ and $R^3$ are the same or different and each represents a hydrogen atom, a halogen atom or an alkyl group which may be substituted with a halogen atom or atoms, $R^4$ represent a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, is a useful compound as an intermediate of sulfonylurea herbicides (e.g. U.S. Pat. No. 4,994,571 and U.S. Pat. No. 5,017,212).

As processes for producing thus sulfonyl chloride compound represented by the formula (2), a process comprising reacting the corresponding pyridazine compound with a sulfonating agent followed by reacting with a chlorinating agent has been known (e.g. US 2005-32650 A).

DISCLOSURE OF THE INVENTION

The present invention provides a process for producing a sulfonyl chloride compound comprising:

(A) a step comprising reacting a pyridazine compound represented by the formula (1):

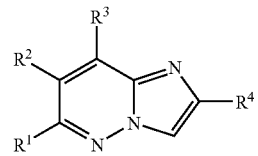

(1)

wherein $R^1$ represents a hydrogen atom, a halogen atom, an alkyl group which may be substituted with a halogen atom or atoms, an alkenyl group which may be substituted with a halogen atom or atoms, an alkynyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, $R^2$ and $R^3$ are the same or different and each represents a hydrogen atom, a halogen atom or an alkyl group which may be substituted with a halogen atom or atoms, $R^4$ represent a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, with a sulfonating agent;

(B) a step comprising contacting the reaction mixture obtained in the step (A) with a chlorinating agent; and (C) a step comprising mixing the reaction mixture obtained in the step (B) with an aqueous inorganic base solution to separate an organic layer containing a sulfonyl chloride compound represented by the formula (2):

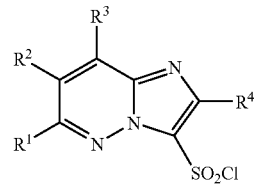

(2)

wherein $R^1$ to $R^4$ are the same meanings as defined above.

BEST MODE FOR CARRYING OUT THE PRESENT INVENTION

First, (A) a step of reacting a pyridazine compound represented by the formula (1):

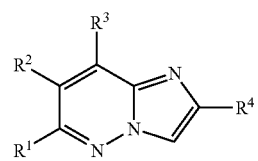

(1)

wherein $R^1$ represents a hydrogen atom, a halogen atom, an alkyl group which may be substituted with a halogen atom or atoms, an alkenyl group which may be substituted with a halogen atom or atoms, an alkynyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, $R^2$ and $R^3$ are the same or different and each represents a hydrogen atom, a halogen atom or an alkyl group which may be substituted with a halogen atom or atoms, $R^4$ represent a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group (hereinafter, simply referred to as the pyridazine compound (1)), with a sulfonating agent (hereinafter, simply referred to as the step (A)) will be illustrated.

In the pyridazine compound (1), examples of the halogen atom include a fluorine atom, a chlorine atom and a bromine atom.

Examples of the alkyl group which may be substituted with a halogen atom or atoms include a C1-C6 linear, branched chain or cyclic unsubstituted alkyl group such a methyl, ethyl, n-propyl, isopropyl, n-butyl, isobutyl, sec-butyl, tert-butyl, n-pentyl, n-hexyl, cyclopentyl and cyclohexyl group; and those wherein at least one hydrogen atom of the above-mentioned unsubstituted alkyl groups is substituted with the above-mentioned halogen atom such as a fluoromethyl, chloromethyl, bromomethyl, trifluoromethyl, 1-chloroethyl, 1-bromoethyl, 1,1,1-trifluoroethyl, 1-chloropropyl, 1-bromopropyl and 1,1,1-trifluoropropyl group.

Examples of the alkenyl group which may be substituted with a halogen atom or atoms include a C2-C6 linear, branched chain or cyclic unsubstituted alkenyl group such as a vinyl, 1-propenyl, 2-propenyl, 2-methyl-1-propenyl, 1,2-propadienyl, 1-butenyl, 2-butenyl, 1,3-butadienyl, 1-pentenyl, 1-hexenyl and 1-cyclohexenyl group; and those wherein at least one hydrogen atom of the above-mentioned unsubstituted alkenyl groups is substituted with the above-mentioned halogen atom such as a 2-chloro-1-propenyl, 2,2-dichlorovinyl, 2-chloro-2-fluorovinyl and 3-bromo-1-methyl-1-propenyl group.

Examples of the alkynyl group which may be substituted with a halogen atom or atoms include a C2-C6 linear or branched chain unsubstituted alkynyl group such as an ethynyl, 1-propynyl, 2-propynyl, 2-butynyl, 2-pentynyl and 4-methyl-2-pentynyl group; and those wherein at least one hydrogen atom of the above-mentioned unsubstituted alkynyl groups is substituted with the above-mentioned halogen atom such as a 3-chloro-1-propynyl and 1-fluoro-2-propynyl group.

Examples of the alkoxy group which may be substituted with a halogen atom or atoms include a C1-C6 linear, branched chain or cyclic unsubstituted alkoxy group such a methoxy, ethoxy, n-propoxy, isopropoxy, n-butoxy, sec-butoxy, tert-butoxy, n-pentyloxy, n-hexyloxy, cyclopropyloxy, cyclopentyloxy and cyclohexyloxy group; and those wherein at least one hydrogen atom of the above-mentioned unsubstituted alkoxy groups is substituted with the above-mentioned halogen atom such as a fluoromethoxy, chloromethoxy, bromomethoxy, trifluoromethoxy, 1-chloroethoxy, 1-bromoethoxy, 1,1,1-trifluoroethoxy, 1-chloropropoxy, 1-bromopropoxy and 1,1,1-trifluoropropoxy group.

Examples of the alkylthio group include those composed of the above-mentioned C1-C6 unsubstituted alkyl group and a sulfur atom such as a methylthio, ethylthio, n-propylthio, isopropylthio, n-butylthio, sec-butylthio, tert-butylthio, n-pentylthio, n-hexylthio, cyclopropylthio, cyclopentylthio and cyclohexylthio group.

Examples of the alkoxycarbonyl group include those composed of the above-mentioned C1-C6 unsubstituted alkoxy group and a carbonyl group such as a methoxycarbonyl, ethoxycarbonyl, n-propoxycarbonyl, isopropoxycarbonyl, n-butoxycarbonyl, sec-butoxycarbonyl, tert-butoxycarbonyl, n-pentyloxycarbonyl, n-hexyloxycarbonyl, cyclopropyloxycarbonyl, cyclopentyloxycarbonyl and cyclohexyloxycarbonyl group.

Examples of the alkylsulfonyl group include those composed of the above-mentioned C1-C6 unsubstituted alkyl group and a sulfonyl group such as a methylsulfonyl, ethylsulfonyl, n-propylsulfonyl, isopropylsulfonyl, n-butylsulfonyl, sec-butylsulfonyl, tert-butylsulfonyl, n-pentylsulfonyl, n-hexylsulfonyl, cyclopropylsulfonyl, cyclopentylsulfonyl and cyclohexylsulfonyl group.

The alkylamino group is an amino group substituted with an alkyl group. Examples thereof include an amino group substituted with the above-mentioned C1-C6 unsubstituted alkyl group such as a methylamino, ethylamino, n-propylamino, isopropylamino, n-butylamino, sec-butylamino, tert-butylamino, n-pentylamino, n-hexylamino, cyclopropylamino, cyclopentylamino and cyclohexylamino group.

The dialkylamino group is an amino group substituted with two above-mentioned unsubstituted alkyl groups and the two unsubstituted alkyl groups may be the same or different. The two unsubstituted alkyl groups may be bonded to form a cyclic amino group together with the nitrogen atom to which they are bonded. Examples of the dialkylamino group include an amino group substituted with two above-mentioned C1-C6 unsubstituted alkyl groups such as a dimethylamino, diethylamino, di-n-propylamino, diisopropylamino, di-n-butylamino, di-n-hexylamino, dicyclopropylamino, dicyclopentylamino, dicyclohexylamino, methylethylamino and ethylisopropylamino group; and a C2-C6 cyclic amino group such as aziridino, pyrrolidino and piperidino group.

Examples of the pyridazine compound (1) include imidazo[1,2-b]pyridazine, 2-chloroimidazo[1,2-b]pyridazine, 2-bromoimidazo[1,2-b]pyridazine, 2-fluoroimidazo[1,2-b]pyridazine, 2-methylimidazo[1,2-b]pyridazine, 2-ethylimidazo[1,2-b]pyridazine, 2-n-propylimidazo[1,2-b]pyridazine, 2-trifluoroimidazo[1,2-b]pyridazine, 2-ethylsulfonylimidazo[1,2-b]pyridazine, 2-cyanoimidazo[1,2-b]pyridazine, 2-methoxyimidazo[1,2-b]pyridazine, 2-ethoxyimidazo[1,2-b]pyridazine, 2-carbamoylimidazo[1,2-b]pyridazine, 6-propylimidazo[1,2-b]pyridazine, 6-isopropylimidazo[1,2-b]pyridazine, 6-n-butylimidazo[1,2-b]pyridazine, 6-ethylimidazo[1,2-b]pyridazine, 6-methylimidazo[1,2-b]pyridazine, 6-ethylthioimidazo[1,2-b]pyridazine, 6-methoxyimidazo[1,2-b]pyridazine, 6-n-propyl-2-chloroimidazo[1,2-b]pyridazine, 6-n-butyl-2-chloroimidazo[1,2-b]pyridazine, 6-isobutyl-2-chloroimidazo[1,2-b]pyridazine, 6-ethyl-2-chloroimidazo[1,2-b]pyridazine, 6-cyclopropyl-2-chloroimidazo[1,2-b]pyridazine, 6-vinyl-2-chloroimidazo[1,2-b]pyridazine, 6-(1-propenyl)-2-chloroimidazo[1,2-b]pyridazine, 6-ethynyl-2-chloroimidazo[1,2-b]pyridazine, 6-n-propyl-2-bromoimidazo[1,2-b]pyridazine, 6-n-butyl-2-bromoimidazo[1,2-b]pyridazine, 6-isobutyl-2-bromoimidazo[1,2-b]pyridazine, 6-ethyl-2-bromoimidazo[1,2-b]pyridazine, 6-cyclopropyl-2-bromoimidazo[1,2-b]pyridazine, 6-vinyl-2-bromoimidazo[1,2-b]pyridazine, 6-(1-propenyl)-2-bromoimidazo[1,2-b]pyridazine, 6-ethynyl-2-bromoimidazo[1,2-b]pyridazine, 6-n-propyl-2-fluoroimidazo[1,2-b]pyridazine, 6-n-butyl-2-fluoroimidazo[1,2-b]pyridazine, 6-isobutyl-2-fluoroimidazo[1,2-b]pyridazine, 6-ethyl-2-fluoroimidazo[1,2-b]pyridazine, 6-cyclopropyl-2-fluoroimidazo[1,2-b]pyridazine, 6-vinyl-2-fluoroimidazo[1,2-b]pyridazine, 6-(1-propenyl)-2-fluoroimidazo[1,2-b]pyridazine, 6-ethynyl-2-fluoroimidazo[1,2-b]pyridazine, 6-n-propyl-2-methylimidazo[1,2-b]pyridazine, 6-isopropyl-2-methylimidazo[1,2-b]pyridazine, 6-ethylthio-2-methylimidazo[1,2-b]pyridazine, 6-n-propyl-2-ethylimidazo[1,2-b]pyridazine, 6-isopropyl-2-ethylimidazo[1,2-b]pyridazine, 2,6-di-n-propylimidazo[1,2-b]pyridazine, 6-n-propyl-2-trifluoromethylimidazo[1,2-b]pyridazine, 6-n-propyl-2-ethylsulfonylimidazo[1,2-b]pyridazine, 6-n-propyl-2-cyanoimidazo[1,2-b]pyridazine, 6-n-propyl-2-methoxyimidazo[1,2-b]pyridazine, 6-n-propyl-2-ethoxycarbonylimidazo[1,2-b]pyridazine, 6-n-propyl-2-carbamoylimidazo[1,2-b]pyridazine, 6-chloro-2,8-dimethylimidazo[1,2-b]pyridazine, 6,7-di-n-propyl-2-chloroimidazo[1,2-b]pyridazine, 6,8-di-n-propyl-2-chloroimidazo[1,2-b]pyridazine, 6,7,8-tri-n-propyl-2-chloroimidazo[1,2-b]pyridazine, 6-n-propyl-2,7-dichloroimidazo[1,2-b]pyridazine, 6-n-propyl-2,8-dichloroimidazo[1,2-b]pyridazine, and 6-n-propyl-2,7,8-trichloroimidazo[1,2-b]pyridazine. The pyridazine compound (1) may be in a form of salt such as a hydrochloric acid salt, a sulfuric acid salt, a hydrobromic acid salt, a nitric acid salt, a phosphoric acid salt and a acetic acid salt.

As the pyridazine compound (1), a commercially available one may be used and one produced according to known methods described, for example, in JP 1-316379 A and US 2005-32650 A may be used.

Examples of the sulfonating agent include chlorosulfonic acid, fuming sulfuric acid and anhydrous sulfuric acid, and chlorosulfonic acid is preferable. As the sulfonating agent, a commercially available one is usually used.

The amount of the sulfonating agent is usually 1 mole or more relative to 1 mole of the pyridazine compound (1), and preferably 2 to 10 moles. The large excess of the sulfonating agent may be used to serve as the solvent.

The reaction of the pyridazine compound (1) and the sulfonating agent is usually conducted by mixing the pyridazine compound (1) and the sulfonating agent. The mixing order is not particularly limited and the pyridazine compound (1) is preferably added to the sulfonating agent.

The reaction may be conducted in the absence of a solvent and in the presence of the solvent. The reaction is preferably conducted in the absence of the solvent.

The solvent is not particularly limited in so far as it is an inert solvent on the reaction. Examples thereof include an aliphatic hydrocarbon solvent such as pentane, hexane, heptane and cyclohexane, and a nitrile solvent such as acetonitrile and propionitrile. The aliphatic hydrocarbon solvent is preferable and a C5-C7 aliphatic hydrocarbon solvent is more preferable. The amount of the solvent is not particularly limited and in the viewpoint of economic efficiency, it is practically 100 parts by weight or less relative to 1 part by weight of the pyridazine compound (1). As described above, the sulfonating agent may be used as the solvent.

The reaction temperature is usually 30 to 150° C., and preferably 80 to 110° C. The reaction temperature is usually 10 minutes to 24 hours.

Since an acidic gas such as $SO_x$ gas generates with the progress of the reaction, the reaction is preferably conducted with removing the acidic gas out of the reaction system. Examples of the method for conducting the reaction with removing the acidic gas out of the reaction system include a process comprising reacting with blowing an inert gas such as nitrogen gas and argon gas into the reaction mixture, and a process comprising reacting with refluxing the reaction mixture.

The congress of the reaction can be confirmed by a conventional analytical means such as gas chromatography and high performance liquid chromatography.

Next, (B) a step comprising contacting the reaction mixture obtained in the step (A) with a chlorinating agent (hereinafter, simply referred to as the step (B)) will be illustrated.

The reaction mixture obtained in the above-mentioned step (A) is usually used in the present step (B) as it is. When the reaction is conducted in the presence of the solvent in the step (A), the solvent may be removed from the reaction mixture and then used.

Examples of the chlorinating agent include thionyl chloride, sulfuryl chloride, phosgene, oxalyl chloride, phosphorus oxychloride, phosphorus pentachloride and phosphorus trichloride, and the chlorinating agent having the boiling point of 90° C. or less at ordinary pressure such as thionyl chloride, sulfuryl chloride, phosgene, oxalyl chloride and phosphorus trichloride is preferable, and thionyl chloride is more preferable. As the chlorinating agent, a commercially available one is usually used. The amount of the chlorinating agent to be used is usually 1 mole or more relative to 1 mole of the pyridazine compound (1) used in the step (A). There is no specific upper limit and the large excess thereof may be used to serve as the reaction solvent. In the viewpoint of economic efficiency, it is practically 100 parts by weight or less relative to 1 part by weight of the pyridazine compound (1) used in the step (A).

In the present step (B), the contact of the reaction mixture obtained in the step (A) and the chlorinating agent is usually conducted by adding the chlorinating agent to the reaction mixture obtained in the step (A). The above-mentioned contact may be conducted in the absence of the solvent and in the presence of the solvent. The contact of the both is preferably conducted in the absence of the solvent.

The solvent is not particularly limited in so far as it is an inert solvent on the reaction. Examples thereof include an aliphatic hydrocarbon solvent such as pentane, hexane, heptane and cyclohexane, and a nitrile solvent such as acetonitrile and propionitrile. The aliphatic hydrocarbon solvent is preferable and a C5-C7 aliphatic hydrocarbon solvent is more preferable. The amount thereof to be used is not particularly limited and in the viewpoint of economic efficiency, it is practically 100 parts by weight or less relative to 1 part by weight of the pyridazine compound (1) used in the step (A).

The reaction mixture obtained in the step (A) may be contacted with the chlorinating agent in the presence of a tertiary amine or a pyridine. Examples of the tertiary amine include triethylamine, tri-n-propylamine, N,N-dimethylaniline and N,N-diethylaniline, and examples of the pyridine include pyridine. The amount of the tertiary amine or the pyridine is usually 0.01 to 2 moles, and preferably 0.05 to 1 mole relative to 1 mole of the pyridazine compound (1) used in the step (A).

The contacting temperature is usually 0 to 120° C., and preferably the boiling point of the chlorinating agent or more and 120° C. or less. The contacting time is usually 10 minutes to 24 hours.

The congress of the reaction can be confirmed by a conventional analytical means such as gas chromatography and high performance liquid chromatography.

Since an acidic gas such as $SO_x$ gas also generates with the progress of the reaction in the present step (B), the reaction is preferably conducted with removing the acidic gas out of the reaction system. Examples of the method for conducting the reaction with removing the acidic gas out of the reaction system include a process comprising reacting with blowing an inert gas such as nitrogen gas and argon gas into the reaction mixture, and a process comprising reacting with refluxing the reaction mixture.

Next, (C) a step comprising mixing the reaction mixture obtained in the step (B) with an aqueous inorganic base solution to separate an organic layer containing a sulfonyl chloride compound represented by the formula (2) (hereinafter, simply referred to as the sulfonyl chloride compound (2)) (hereinafter, simply referred to as the step (C)) will be illustrated.

The reaction mixture obtained in the above-mentioned step (B) may be used as it is and may be used after concentrating it. When the reaction is conducted in the absence of the solvent in the step (B), the present step (C) is preferably conducted by mixing a water-nonmiscible solvent with the reaction mixture in the viewpoint of the separating property on separating the organic layer containing the sulfonyl chloride compound (2).

Examples of the water-nonmiscible solvent include an aromatic hydrocarbon solvent such as toluene, xylene, mesitylene, chlorobenzene and dichlorobenzene, and an aliphatic hydrocarbon solvent such as pentane, hexane, heptane and cyclohexane. The amount thereof is not particularly limited and in the viewpoint of economic efficiency, it is practically 100 parts by weight or less relative to 1 part by weight of the pyridazine compound (1) used in the step (A).

Examples of the inorganic base include an alkali metal hydroxide such as sodium hydroxide and potassium hydroxide, an alkali metal carbonate such as sodium carbonate and potassium carbonate, an alkaline earth metal carbonate such as calcium carbonate, and an alkali metal hydrogen carbonate such as sodium hydrogen carbonate. The concentration of the inorganic base in the aqueous inorganic base solution is not particularly limited.

The aqueous inorganic base solution is usually used in an amount that pH of the aqueous layer on separating the organic layer containing the sulfonyl chloride compound (2) becomes in a range of 0 to 5, and preferably in a range of 0 to 2.

The mixing temperature of the reaction mixture obtained in the step (B) and the aqueous inorganic base solution is usually 5 to 50° C. The mixing order is not particularly limited and it is preferred that the above-mentioned reaction mixture and the aqueous inorganic base solution are added simultaneously into the container and mixed. It is also preferred that a pH buffer solution is previously added into the container and the above-mentioned reaction mixture and the aqueous inorganic base solution are added simultaneously thereto and mixed. The pH buffer solution is an aqueous solution of the pH buffer agent and examples of the pH buffer agent include an acid such as carbonic acid, phosphoric acid, acetic acid, citric acid, tartaric acid and malic acid, a salt such as sodium salt thereof, potassium salt thereof and ammonium salt thereof. The concentration of the pH buffer agent in the pH buffer solution is not particularly limited in so far as it is in a range wherein the solution shows a buffer action. The amount thereof is not particularly limited.

The mixing time of the reaction mixture obtained in the step (B) and the aqueous inorganic base solution is not particularly limited.

The organic layer containing the sulfonyl chloride compound (2) can be obtained by mixing the reaction mixture obtained in the step (B) with the aqueous inorganic base solution followed by standing for the predetermined time and separating the organic layer containing the sulfonyl chloride compound (2) and the aqueous layer. When it is difficult to separate the organic layer and the aqueous layer, the filter aid may be added to the mixture of the organic layer containing the sulfonyl chloride compound (2) and the aqueous layer, and the resultant mixture may be stirred for the predetermined time and left, and the filter aid may be removed by filtration and the organic layer and the aqueous layer may be separated. Examples of the filter aid include Celite (registered trademark), Radiolite (registered trademark) and alumina. The amount thereof is not particularly limited.

The sulfonyl chloride compound (2) can be isolated by, if necessary, washing the organic layer containing the sulfonyl chloride compound (2) obtained with water or an aqueous acid solution, and concentrating. The sulfonyl chloride compound (2) isolated may be further purified by a conventional means such as distillation and recrystallization.

Examples of the sulfonyl chloride compound (2) include imidazo[1,2-b]pyridazin-3-ylsulfonyl chloride, 2-chloroimidazo[1,2-b]pyridazin-3-ylsulfonyl chloride, 2-bromoimidazo[1,2-b]pyridazin-3-ylsulfonyl chloride, 2-fluoroimidazo[1,2-b]pyridazin-3-ylsulfonyl chloride, 2-methylimidazo[1,2-b]pyridazin-3-ylsulfonyl chloride, 2-ethylimidazo[1,2-b]pyridazin-3-ylsulfonyl chloride, 2-n-propylimidazo[1,2-b]pyridazin-3-ylsulfonyl chloride, 2-trifluoroimidazo[1,2-b]pyridazin-3-ylsulfonyl chloride, 2-ethylsulfonylimidazo[1,2-b]pyridazin-3-ylsulfonyl chloride, 2-cyanoimidazo[1,2-b]pyridazin-3-ylsulfonyl chloride, 2-methoxyimidazo[1,2-b]pyridazin-3-ylsulfonyl chloride, 2-ethoxycarbonylimidazo[1,2-b]pyridazin-3-ylsulfonyl chloride, 2-carbamoylimidazo[1,2-b]pyridazin-3-ylsulfonyl chloride, 6-n-propylimidazo[1,2-b]pyridazin-3-ylsulfonyl chloride, 6-isopropylimidazo[1,2-b]pyridazin-3-ylsulfonyl chloride, 6-n-butylimidazo[1,2-b]pyridazin-3-ylsulfonyl chloride, 6-ethylimidazo[1,2-b]pyridazin-3-ylsulfonyl chloride, 6-methylimidazo[1,2-b]pyridazin-3-ylsulfonyl chloride, 6-ethylthioimidazo[1,2-b]pyridazin-3-ylsulfonyl chloride, 6-methoxyimidazo[1,2-b]pyridazin-3-ylsulfonyl chloride, 6-n-propyl-2-chloroimidazo[1,2-b]pyridazin-3-ylsulfonyl chloride, 6-n-butyl-2-chloroimidazo[1,2-b]pyridazin-3-ylsulfonyl chloride, 6-isobutyl-2-chloroimidazo[1,2-b]pyridazin-3-ylsulfonyl chloride, 6-ethyl-2-chloroimidazo[1,2-b]pyridazin-3-ylsulfonyl chloride, 6-cyclopropyl-2-chloroimidazo[1,2-b]pyridazin-3-ylsulfonyl chloride, 6-vinyl-2-chloroimidazo[1,2-b]pyridazin-3-ylsulfonyl chloride, 6-(1-propenyl)-2-chloroimidazo[1,2-b]pyridazin-3-ylsulfonyl chloride, 6-ethynyl-2-chloroimidazo[1,2-b]pyridazin-3-ylsulfonyl chloride, 6-n-propyl-2-bromoimidazo[1,2-b]pyridazin-3-ylsulfonyl chloride, 6-n-butyl-2-bromoimidazo[1,2-b]pyridazin-3-ylsulfonyl chloride, 6-isobutyl-2-bromoimidazo[1,2-b]pyridazin-3-ylsulfonyl chloride, 6-ethyl-2-bromoimidazo[1,2-b]pyridazin-3-ylsulfonyl chloride, 6-cyclopropyl-2-bromoimidazo[1,2-b]pyridazin-3-ylsulfonyl chloride, 6-vinyl-2-bromoimidazo[1,2-b]pyridazin-3-ylsulfonyl chloride, 6-(1-propenyl)-2-bromoimidazo[1,2-b]pyridazin-3-ylsulfonyl chloride, 6-ethynyl-2-bromoimidazo[1,2-b]pyridazin-3-ylsulfonyl chloride, 6-n-propyl-2-fluoroimidazo[1,2-b]pyridazin-3-ylsulfonyl chloride, 6-n-butyl-2-fluoroimidazo[1,2-b]pyridazin-3-ylsulfonyl chloride, 6-isobutyl-2-fluoroimidazo[1,2-b]pyridazin-3-ylsulfonyl chloride, 6-ethyl-2-fluoroimidazo[1,2-b]pyridazin-3-ylsulfonyl chloride, 6-cyclopropyl-2-fluoroimidazo[1,2-b]pyridazin-3-ylsulfonyl chloride, 6-vinyl-2-fluoroimidazo[1,2-b]pyridazin-3-ylsulfonyl chloride, 6-(1-propenyl)-2-fluoroimidazo[1,2-b]pyridazin-3-ylsulfonyl chloride, 6-ethynyl-2-fluoroimidazo[1,2-b]pyridazin-3-ylsulfonyl chloride, 6-n-propyl-2-methylimidazo[1,2-b]pyridazin-3-ylsulfonyl chloride, 6-isopropyl-2-methylimidazo[1,2-b]pyridazin-3-ylsulfonyl chloride, 6-ethylthio-2-methylimidazo[1,2-b]pyridazin-3-ylsulfonyl chloride, 6-n-propyl-2-ethylimidazo[1,2-b]pyridazin-3-ylsulfonyl chloride, 6-isopropyl-2-ethylimidazo[1,2-b]pyridazin-3-ylsulfonyl chloride, 2,6-di-n-propylimidazo[1,2-b]pyridazin-3-ylsulfonyl chloride, 6-n-propyl-2-trifluoroimidazo[1,2-b]pyridazin-3-ylsulfonyl chloride, 6-n-propyl-2-ethylsulfonylimidazo[1,2-b]pyridazin-3-ylsulfonyl chloride, 6-n-propyl-2-cyanoimidazo[1,2-b]pyridazin-3-ylsulfonyl chloride, 6-n-propyl-2-methoxyimidazo[1,2-b]pyridazin-3-ylsulfonyl chloride, 6-n-propyl-2-ethoxycarbonylimidazo[1,2-b]pyridazin-3-ylsulfonyl chloride, 6-n-propyl-2-carbamoylimidazo[1,2-b]pyridazin-3-ylsulfonyl chloride, 6-chloro-2,8-dimethylimidazo[1,2-b]pyridazin-3-ylsulfonyl chloride, 6,7-di-n-propyl-2-chloroimidazo[1,2-b]pyridazin-3-ylsulfonyl chloride, 6,8-di-n-propyl-2-chloroimidazo[1,2-b]pyridazin-3-ylsulfonyl chloride, 6,7,8-tri-n-propyl-2-chloroimidazo[1,2-b]pyridazin-3-ylsulfonyl chloride, 6-n-propyl-2,7-dichloroimidazo[1,2-b]pyridazin-3-ylsulfonyl chloride, 6-n-propyl-2,8-dichloroimidazo[1,2-b]pyridazin-3-ylsulfonyl chloride, and 6-n-propyl-2,7,8-trichloroimidazo[1,2-b]pyridazin-3-ylsulfonyl chloride.

The sulfonamide compound represented by the formula (3):

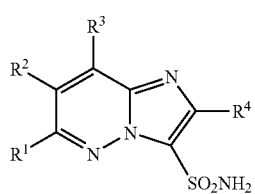

wherein $R^1$ to $R^4$ are the same meanings as defined above (hereinafter, simply referred to as the sulfonamide compound (3)), which is useful as an intermediate of sulfonylurea herbicides, can be produced by reacting the sulfonyl chloride compound (2) thus obtained with ammonia.

The process for producing the sulfonamide compound (3) will be illustrated below.

The organic layer containing the sulfonyl chloride compound (2) obtained in the step (C) may be used as it is, and the sulfonyl chloride compound (2) may be isolated from the organic layer to be used. The sulfonamide compound (3) can be produced in a good yield even though the organic layer is used as it is. The sulfonamide compound (3) can also be produced in a good yield by using the sulfonyl chloride compound (2) isolated without purifying by a conventional means such as column chromatography.

As ammonia, an aqueous ammonia water may be used and ammonia gas may be used. Ammonia gas is preferably used. When the aqueous ammonia water is used, the concentration thereof is not particularly limited and conc. aqueous ammonia water is preferably used.

The amount of ammonia to be used is usually 1 mole or more relative to 1 mole of the sulfonyl chloride compound (2), and there is no specific upper limit. When the aqueous ammonia water is used as ammonia, it is preferably 10 moles or less relative to 1 mole of the sulfonyl chloride compound (2).

The reaction of the sulfonyl chloride compound (2) and ammonia is usually conducted in an inert solvent on the reaction. Examples of the inert solvent on the reaction include water; an ether solvent such as diethyl ether and tetrahydrofuran; an aromatic hydrocarbon solvent such as toluene, xylene, mesitylene, chlorobenzene and dichlorobenzene; an aliphatic hydrocarbon solvent such as pentane, hexane, heptane and cyclhexane; a nitrile solvent such as acetonitrile and propionitrile; and an alcohol solvent such as methanol and ethanol. The inert solvents may be used alone and in a form of mixture.

The reaction temperature is usually −60 to 100° C. The reaction time is usually 0.5 to 24 hours.

The reaction may be conducted under ordinary pressure condition and under pressurized condition.

The progress of the reaction can be confirmed by a conventional analytical means such as gas chromatography and high performance liquid chromatography.

After completion of the reaction, for example, the sulfonamide compound (3) can be isolated as the solid by, if necessary, adding water to the reaction mixture, conducting neutralization, and filtrating. The sulfonamide compound (3) isolated may be further purified, for example, by a conventional purification means such as washing and recrystallization.

Examples of the sulfonamide compound (3) include
imidazo[1,2-b]pyridazin-3-ylsulfonamide,
2-chloro-imidazo[1,2-b]pyridazin-3-ylsulfonamide,
2-bromoimidazo[1,2-b]pyridazin-3-ylsulfonamide,
2-fluoroimidazo[1,2-b]pyridazin-3-ylsulfonamide,
2-methylimidazo[1,2-b]pyridazin-3-ylsulfonamide,
2-ethylimidazo[1,2-b]pyridazin-3-ylsulfonamide,
2-n-propylimidazo[1,2-b]pyridazin-3-ylsulfonamide,
2-trifluoroimidazo[1,2-b]pyridazin-3-ylsulfonamide,
2-ethylsulfonylimidazo[1,2-b]pyridazin-3-ylsulfonamide,
2-cyanoimidazo[1,2-b]pyridazin-3-ylsulfonamide,
2-methoxyimidazo[1,2-b]pyridazin-3-ylsulfonamide,
2-ethoxycarbonylimidazo[1,2-b]pyridazin-3-ylsulfonamide,
2-carbamoylimidazo[1,2-b]pyridazin-3-ylsulfonamide,
6-n-propylimidazo[1,2-b]pyridazin-3-ylsulfonamide,
6-isopropylimidazo[1,2-b]pyridazin-3-ylsulfonamide,
6-n-butylimidazo[1,2-b]pyridazin-3-ylsulfonamide,
6-ethylimidazo[1,2-b]pyridazin-3-ylsulfonamide,
6-methylimidazo[1,2-b]pyridazin-3-ylsulfonamide,
6-ethylthioimidazo[1,2-b]pyridazin-3-ylsulfonamide,
6-methoxyimidazo[1,2-b]pyridazin-3-ylsulfonamide,
6-n-propyl-2-chloroimidazo[1,2-b]pyridazin-3-ylsulfonamide,
6-n-butyl-2-chloroimidazo[1,2-b]pyridazin-3-ylsulfonamide,
6-isobutyl-2-chloroimidazo[1,2-b]pyridazin-3-ylsulfonamide,
6-ethyl-2-chloroimidazo[1,2-b]pyridazin-3-ylsulfonamide,
6-cyclopropyl-2-chloroimidazo[1,2-b]pyridazin-3-ylsulfonamide,
6-vinyl-2-chloroimidazo[1,2-b]pyridazin-3-ylsulfonamide,
6-(1-propenyl)-2-chloroimidazo[1,2-b]pyridazin-3-ylsulfonamide,
6-ethynyl-2-chloroimidazo[1,2-b]pyridazin-3-ylsulfonamide,
6-n-propyl-2-bromoimidazo[1,2-b]pyridazin-3-ylsulfonamide,
6-n-butyl-2-bromoimidazo[1,2-b]pyridazin-3-ylsulfonamide,
6-isobutyl-2-bromoimidazo[1,2-b]pyridazin-3-ylsulfonamide,
6-ethyl-2-bromoimidazo[1,2-b]pyridazin-3-ylsulfonamide,
6-cyclopropyl-2-bromoimidazo[1,2-b]pyridazin-3-ylsulfonamide,
6-vinyl-2-bromoimidazo[1,2-b]pyridazin-3-ylsulfonamide, 6-(1-propenyl)-2-bromoimidazo[1,2-b]pyridazin-3-ylsulfonamide,
6-ethynyl-2-bromoimidazo[1,2-b]pyridazin-3-ylsulfonamide,
6-n-propyl-2-fluoroimidazo[1,2-b]pyridazin-3-ylsulfonamide,
6-n-butyl-2-fluoroimidazo[1,2-b]pyridazin-3-ylsulfonamide,
6-isobutyl-2-fluoroimidazo[1,2-b]pyridazin-3-ylsulfonamide,
6-ethyl-2-fluoroimidazo[1,2-b]pyridazin-3-ylsulfonamide,
6-cyclopropyl-2-fluoroimidazo[1,2-b]pyridazin-3-ylsulfonamide,
6-vinyl-2-fluoroimidazo[1,2-b]pyridazin-3-ylsulfonamide,
6-(1-propenyl)-2-fluoroimidazo[1,2-b]pyridazin-3-ylsulfonamide,
6-ethynyl-2-fluoroimidazo[1,2-b]pyridazin-3-ylsulfonamide,
6-n-propyl-2-methylimidazo[1,2-b]pyridazin-3-ylsulfonamide,
6-isopropyl-2-methylimidazo[1,2-b]pyridazin-3-ylsulfonamide,
6-ethylthio-2-methylimidazo[1,2-b]pyridazin-3-ylsulfonamide,
6-n-propyl-2-ethylimidazo[1,2-b]pyridazin-3-ylsulfonamide,
6-isopropyl-2-ethylimidazo[1,2-b]pyridazin-3-ylsulfonamide,
2,6-di-n-propylimidazo[1,2-b]pyridazin-3-ylsulfonamide,
6-n-propyl-2-trifluoroimidazo[1,2-b]pyridazin-3-ylsulfonamide,
6-n-propyl-2-ethylsulfonylimidazo[1,2-b]pyridazin-3-ylsulfonamide,
6-n-propyl-2-cyanoimidazo[1,2-b]pyridazin-3-ylsulfonamide,
6-n-propyl-2-methoxyimidazo[1,2-b]pyridazin-3-ylsulfonamide,
6-n-propyl-2-ethoxycarbonylimidazo[1,2-b]pyridazin-3-ylsulfonamide,
6-n-propyl-2-carbamoylimidazo[1,2-b]pyridazin-3-ylsulfonamide,
6-chloro-2,8-dimethylimidazo[1,2-b]pyridazin-3-ylsulfonamide,
6,7-di-n-propyl-2-chloroimidazo[1,2-b]pyridazin-3-ylsulfonamide,
6,8-di-n-propyl-2-chloroimidazo[1,2-b]pyridazin-3-ylsulfonamide,
6,7,8-tri-n-propyl-2-chloroimidazo[1,2-b]pyridazin-3-ylsulfonamide,
6-n-propyl-2,7-dichloroimidazo[1,2-b]pyridazin-3-ylsulfonamide,
6-n-propyl-2,8-dichloroimidazo[1,2-b]pyridazin-3-ylsulfonamide, and
6-n-propyl-2,7,8-trichloroimidazo[1,2-b]pyridazin-3-ylsulfonamide.

EXAMPLES

The present invention will be further illustrated by Examples in detail below, but the present invention is not limited by these Examples. The analysis was conducted using the high performance liquid chromatography method. The content was calculated by the high performance liquid chromatography internal standard method, and the purity was calculated by the high performance liquid chromatography percentage method.

Reference Example 1

Into a 500 mL four-necked separable flask purged with nitrogen, 20.17 g of 2,6-dichloroimidazo[1,2-b]pyridazine (content: 99.2% by weight) and 190.5 g of xylene were charged to prepare a xylene solution containing 2,6-dichloroimidazo[1,2-b]pyridazine. The solution obtained by mixing 4 mL of xylene and 0.22 g of 1,3-bis(diphenylphosphino)propane and 0.62 g of a toluene solution of nickel naphthenate (II) (content: 5% by weight) were mixed to prepare a solution containing a nickel catalyst. The xylene solution containing 2,6-dichloroimidazo[1,2-b]pyridazine and the solution containing a nickel catalyst were mixed, and to the resultant mixture, 63.4 g of a tetrahydrofuran solution of n-propylmagnesium bromide (content: 22.2% by weight) was added dropwise over about 2 hours at an inner temperature of 20 to 30° C. to effect reaction. After completion of the reaction, the reaction mixture was added dropwise into a mixture of 40.4 g of 3% by weight aqueous sulfuric acid solution and 1 g of Radiolite (which was manufactured by Showa Chemical Industry Co., LTD.). After that, the resultant mixture was stirred and filtrated. The organic layer was separated from the filtrate obtained and washed twice with about 40 g of water. The organic layer after washing was concentrated to obtain 20.9 g of 6-n-propyl-2-chloroimidazo[1,2-b]pyridazine (purity: 93.2%). Yield: 94%

Reference Example 2

Into a 500 mL reaction container purged with nitrogen, 20.4 g of 2,6-dichloroimidazo[1,2-b]pyridazine (content: 92% by weight), 150 mL of toluene and 0.27 g of 1,3-bis(diphenylphosphino)propanenickel chloride (II) (content: 94% by weight) were charged, and 50 mL of a tetrahydrofuran solution of n-propylmagnesium bromide (concentration: 2 mole/L) was added dropwise thereto at 20 to 30° C. to effect reaction. After completion of the reaction, the reaction mixture was added dropwise into 75 g of 10% by weight aqueous sulfuric acid solution. The resultant mixture was stirred and left, and the organic layer was separated. The organic layer was washed with 10% by weight aqueous sulfuric acid solution, 5% by weight aqueous sodium carbonate solution and water followed by concentrating to obtain 20.7 g of 6-n-propyl-2-chloroimidazo[1,2-b]pyridazine (purity: 94.0%). Yield: 99%

Example 1

Into a 200 mL four-necked flask equipped with a condenser, 52.6 g of chlorosulfonic acid was charged and heated to an inner temperature of 65° C. To this, 30 g of 6-n-propyl-2-chloroimidazo[1,2-b]pyridazine, which was produced according to a similar method as Reference Example 1, was melted and added dropwise at an inner temperature of 65 to 85° C., and the resultant mixture was reacted at an inner temperature of 100° C. for 1 hour.

To the resultant mixture, 45 g of thionyl chloride was added dropwise at an inner temperature of 100° C., and reacted at the same temperature for 4 hours. The resultant reaction mixture was cooled to room temperature, and 194 g of xylene was added thereto to obtain a xylene solution.

To a mixture of 97 g of 2% by weight aqueous sodium dihydrogenphosphate solution and 7.8 g of Radiolite (registered trademark; manufactured by Showa Chemical Industry Co., LTD) of which inner temperature was adjusted at 10° C., the xylene solution obtained above and 29% by weight aqueous sodium hydroxide solution were added simultaneously while keeping at an inner temperature of 5 to 15° C. and pH of 0 to 2. The amount of the aqueous sodium hydroxide solution to be used was 92 g and pH of the aqueous layer after completion of the addition was 0.5. The mixture was stirred at an inner temperature of 10 to 15° C. for 30 minutes and Radiolite was removed by filtration. After that, the organic layer was separated and washed with 116 g of 5% by weight aqueous sulfuric acid solution. From the organic layer obtained, 80 g of xylene was distilled away together with water (inner temperature of 40 to 75° C./10.7 MPa) to obtain 255.2 g of a solution containing 6-n-propyl-2-chloroimidazo[1,2-b]pyridazin-3-ylsulfonyl chloride. The content of 6-n-propyl-2-chloroimidazo[1,2-b]pyridazin-3-ylsulfonyl chloride in the solution was 16.0% by weight. Purity: 93.2%. Yield: 97% (based on 6-n-propyl-2-chloroimidazo[1,2-b]pyridazine)

Into a 500 mL separable flask, 200 g of the solution containing 6-n-propyl-2-chloroimidazo[1,2-b]pyridazin-3-ylsulfonyl chloride obtained in the above and 16.4 g of tetrahydrofuran were charged, and 8.2 L of ammonia gas was blew therein at an inner temperature of 17 to 23° C. over 12 hours and then, stirred further for 4 hours to effect reaction.

To the reaction mixture obtained, 108 g of water was charged and heated to an inner temperature of 40° C. The resultant mixture was stirred at the same temperature for 1 hour and then, cooled to an inner temperature of 10° C. and stirred at the same temperature for 1 hour. To the mixture, 18 g of 20% by weight aqueous sulfuric acid solution was added dropwise to adjust pH thereof to 6.0 to 7.5.

The mixture was filtrated to obtain crude solids of 6-n-propyl-2-chloroimidazo[1,2-b]pyridazin-3-ylsulfonamide. The solids obtained were washed with 72 g of xylene, 72 g of 50% by weight aqueous methanol solution and 108 g of water, and dried (inner temperature of 90 to 100° C.) under reduced pressure (6.7 kPa) to obtain 32.7 g of 6-n-propyl-2-chloroimidazo[1,2-b]pyridazin-3-ylsulfonamide in a form of pale brown powder. Purity: 97.8%. Yield: 95% (based on 6-n-propyl-2-chloroimidazo[1,2-b]pyridazin-3-ylsulfonyl chloride)

Example 2

Into a 50 mL four-necked flask equipped with a condenser, 1.5 g of chlorosulfonic acid was charged and heated to an inner temperature of 65° C. To this, 30 g of 6-n-propyl-2-chloroimidazo[1,2-b]pyridazine obtained in Reference Example 1 was melted and added dropwise at an inner temperature of 65 to 85° C., and then, the resultant mixture was reacted at an inner temperature of 85° C. for 2 hour while nitrogen gas was blew therein.

The resultant reaction mixture was heated to an inner temperature of 100° C., and 3.3 g of thionyl chloride was added dropwise thereto at an inner temperature of 100° C., and reacted at the same temperature for 20 hours. The resultant reaction mixture was cooled to room temperature, and 8 g of xylene was added thereto to obtain a xylene solution.

To a mixture of 5 g of 2% by weight aqueous sodium dihydrogenphosphate solution and 0.2 g of Radiolite (registered trademark; manufactured by Showa Chemical Industry Co., LTD) of which inner temperature was adjusted at 10° C., the xylene solution obtained above and 29% by weight aqueous sodium hydroxide solution were added simultaneously while keeping at an inner temperature of 5 to 15° C. and pH of 0 to 2. The amount of the aqueous sodium hydroxide solution to be used was 0.3 g and pH thereof after completion of the addition was 0.5. The mixture was stirred at an inner temperature of 10 to 15° C. for 30 minutes and Radiolite was removed by filtration. After that, the organic layer was separated and washed with 15 g of 5% by weight aqueous sulfuric acid solution. From the organic layer obtained, 2 g of xylene was distilled away together with water (inner temperature of 40 to 75° C./10.7 MPa) to obtain 8.5 g of a solution containing 6-n-propyl-2-chloroimidazo[1,2-b]pyridazin-3-ylsulfonyl chloride. The content of 6-n-propyl-2-chloroimidazo[1,2-b]pyridazin-3-ylsulfonyl chloride in the solution was 16.1% by weight. Purity: 93%. Yield: 98% (based on 6-n-propyl-2-chloroimidazo[1,2-b]pyridazine)

Example 3

Into a 200 mL four-necked flask equipped with a condenser, 9.6 g of chlorosulfonic acid was charged and heated to an inner temperature of 65° C. To this, 5.4 g of 6-n-propyl-2-chloroimidazo[1,2-b]pyridazine obtained in Reference Example 1 was melted and added dropwise at an inner temperature of 65 to 85° C., and then, the resultant mixture was reacted at an inner temperature of 100° C. for 1 hour.

To this, 10.1 g of phosphorus oxychloride was added dropwise thereto at an inner temperature of 100° C., and reacted at the same temperature for 4 hours. The resultant reaction mixture was cooled to room temperature, and 37.6 g of xylene was added thereto to obtain a xylene solution.

To a mixture of 18.8 g of 2% by weight aqueous sodium dihydrogenphosphate solution and 1.5 g of Radiolite (registered trademark; manufactured by Showa Chemical Industry Co., LTD) of which inner temperature was adjusted at 10° C., the xylene solution obtained above and 29% by weight aqueous sodium hydroxide solution were added simultaneously while keeping at an inner temperature of 5 to 15° C. and pH of 0 to 2. The amount of the aqueous sodium hydroxide solution to be used was 20.5 g and pH thereof after completion of the addition was 0.3. The mixture was stirred at an inner temperature of 10 to 15° C. for 30 minutes and Radiolite was removed by filtration. After that, the organic layer was separated and washed with 116 g of 5% by weight aqueous sulfuric acid solution. From the organic layer obtained, 7.6 g of xylene was distilled away together with water (inner temperature of 40 to 75° C./10.7 MPa) to obtain 43.2 g of a solution containing 6-n-propyl-2-chloroimidazo[1,2-b]pyridazin-3-ylsulfonyl chloride. The content of 6-n-propyl-2-chloroimidazo[1,2-b]pyridazin-3-ylsulfonyl chloride in the solution was 15.6% by weight. Purity: 90.3%. Yield: 89% (based on 6-n-propyl-2-chloroimidazo[1,2-b]pyridazine)

Example 4

Into a 200 mL four-necked flask equipped with a condenser, 9.6 g of chlorosulfonic acid was charged and heated to an inner temperature of 65° C. To this, 5.4 g of 6-n-propyl-2-chloroimidazo[1,2-b]pyridazine obtained in Reference Example 1 was melted and added dropwise at an inner temperature of 65 to 85° C., and then, the resultant mixture was reacted at an inner temperature of 100° C. for 1 hour.

To this, 8.7 g of oxalyl chloride was added dropwise thereto at an inner temperature of 100° C., and reacted at the same temperature for 4 hours. The resultant reaction mixture was cooled to room temperature, and 37.6 g of xylene was added thereto to obtain a xylene solution.

To a mixture of 18.8 g of 2% by weight aqueous sodium dihydrogenphosphate solution and 1.5 g of Radiolite (registered trademark; manufactured by Showa Chemical Industry Co., LTD) of which inner temperature was adjusted at 10° C., the xylene solution obtained above and 29% by weight aqueous sodium hydroxide solution were added simultaneously while keeping at an inner temperature of 5 to 15° C. and pH of 0 to 2. The amount of the aqueous sodium hydroxide solution to be used was 15.9 g and pH thereof after completion of the addition was 0.4. The mixture was stirred at an inner temperature of 10 to 15° C. for 30 minutes and Radiolite was removed by filtration. After that, the organic layer was separated and washed with 116 g of 5% by weight aqueous sulfuric acid solution. From the organic layer obtained, 7.1 g of xylene was distilled away together with water (inner temperature of 40 to 75° C./10.7 MPa) to obtain 43.8 g of a solution containing 6-n-propyl-2-chloroimidazo[1,2-b]pyridazin-3-ylsulfonyl chloride. The content of 6-n-propyl-2-chloroimidazo[1,2-b]pyridazin-3-ylsulfonyl chloride in the solution was 16.1% by weight. Purity: 92.8%. Yield: 94% (based on 6-n-propyl-2-chloroimidazo[1,2-b]pyridazine)

Example 5

Into a 500 mL separable flask, 16.8 g of tetrahydrofuran was charged and 200 g of the solution containing 6-n-propyl-2-chloroimidazo[1,2-b]pyridazin-3-ylsulfonyl chloride (content: 16.0% by weight), which was obtained according to a similar method as the above-mentioned Example 1, was added dropwise over 12 hours at an inner temperature of 17 to 23° C. and 8.2 L of ammonia gas was simultaneously blew therein over 12 hours. After completion of the addition of the solution containing 6-n-propyl-2-chloroimidazo[1,2-b]pyridazin-3-ylsulfonyl chloride, 7.2 L of ammonia gas was further blew into the reaction liquid over 12 hours.

To the reaction mixture obtained, 108 g of water was charged and heated to an inner temperature of 40° C. The resultant mixture was stirred at the same temperature for 1 hour and then, cooled to an inner temperature of 10° C. and stirred at the same temperature for 1 hour. To the mixture, 24 g of 20% by weight aqueous sulfuric acid solution was added dropwise to adjust pH thereof to 6.0 to 7.5.

The mixture was filtrated to obtain crude 6-n-propyl-2-chloroimidazo[1,2-b]pyridazin-3-ylsulfonamide as solids. The solids obtained were washed with 72 g of xylene, 72 g of 50% by weight aqueous methanol solution and 108 g of water, and dried under reduced pressure (inner temperature 90 to 100° C./6.7 kPa) to obtain 34.8 g of 6-n-propyl-2-chloroimidazo[1,2-b]pyridazin-3-ylsulfonamide in a form of pale brown powder. Purity: 93.8%. Yield: 93% (based on 6-n-propyl-2-chloroimidazo[1,2-b]pyridazin-3-ylsulfonyl chloride)

Example 6

Into a 200 mL four-necked flask equipped with a condenser, 160.1 g of chlorosulfonic acid was charged and heated to an inner temperature of 65° C. To this, 53.8 g of 6-n-propyl-2-chloroimidazo[1,2-b]pyridazine obtained according to a similar method as Reference Example 1 was melted and added dropwise at an inner temperature of 65 to 85° C., and then, the resultant mixture was reacted at an inner temperature of 100° C. for 1 hour.

To this, 58.9 g of thionyl chloride was added dropwise thereto at an inner temperature of 100° C., and reacted at the same temperature for 8 hours. The resultant reaction mixture was cooled to room temperature, and 376.3 g of xylene was added thereto to obtain a xylene solution. The yield of 6-n-propyl-2-chloroimidazo[1,2-b]pyridazin-3-ylsulfonyl chloride: 98% (based on 6-n-propyl-2-chloroimidazo[1,2-b]pyridazine)

To a mixture of 225.8 g of 2% by weight aqueous sodium dihydrogenphosphate solution of which inner temperature was adjusted at 10° C., the xylene solution obtained above and 29% by weight aqueous sodium hydroxide solution were added simultaneously while keeping at an inner temperature of 5 to 15° C. and pH of 0 to 2. The amount of the aqueous sodium hydroxide solution to be used was 261.3 g and pH thereof after completion of the addition was 1.0. The mixture was stirred at an inner temperature of 10 to 15° C. for 30 minutes and Radiolite was removed by filtration. After that, the organic layer was separated and washed with 225.8 g of 10% by weight aqueous sulfuric acid solution to obtain the organic layer containing 6-n-propyl-2-chloroimidazo[1,2-b]pyridazin-3-ylsulfonyl chloride.

INDUSTRIAL APPLICABILITY

According to the present invention, sulfonyl chloride compound, which is useful as an intermediate of sulfonylurea harbicides, can be produced in a good yield. The sulfonamide compound can also be produced in a good yield from the sulfonyl chloride compound obtained.

The invention claimed is:
1. A process for producing a sulfonyl chloride compound comprising:
(A) a step comprising reacting a pyridazine compound represented by the formula (1):

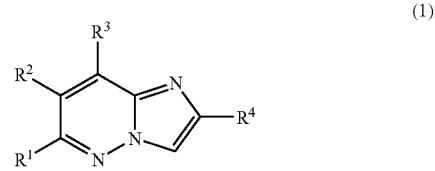

wherein $R^1$ represents a hydrogen atom, a halogen atom, an alkyl group which may be substituted with a halogen atom or atoms, an alkenyl group which may be substituted with a halogen atom or atoms, an alkynyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, $R^2$ and $R^3$ are the same or different and each represents a hydrogen atom, a halogen atom or an alkyl group which may be substituted with a halogen atom or atoms, $R^4$ represent a hydrogen atom, a halogen atom, an alkyl group which may be substituted with a halogen atom or atoms, an alkenyl group which may be substituted with a halogen atom or atoms, an alkoxy group which may be substituted with a halogen atom or atoms, an alkylthio group, an alkylsulfonyl group, an alkoxycarbonyl group, a cyano group, a nitro group, a carbamoyl group, an amino group, an alkylamino group or a dialkylamino group, with a sulfonating agent selected from the group consisting of chlorosulfonic acid, fuming sulfuric acid and anhydrous sulfuric acid;
(B) a step comprising contacting the reaction mixture obtained in the step (A) with a chlorinating agent selected from the group consisting of thionyl chloride, sulfuryl chloride, phosgene, oxalyl chloride, phosphorus oxychloride, phosphorus pentachloride and phosphorus trichloride; and
(C) a step comprising mixing the reaction mixture obtained in the step (B) with an aqueous inorganic base solution to separate an aqueous layer and an organic layer containing a sulfonyl chloride compound represented by the formula (2), wherein the inorganic base is an alkali metal hydroxide, an alkali metal carbonate, an alkaline earth metal carbonate or an alkali metal hydrogen carbonate:

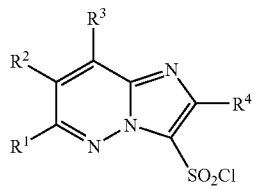

(2)

wherein $R^1$ to $R^4$ are the same meanings as defined above.

2. The process for producing a sulfonyl chloride compound according to claim 1, wherein the sulfonating agent is chlorosulfonic acid in the step (A).

3. The process for producing a sulfonyl chloride compound according to claim 1, wherein the reaction is conducted in the absence of a solvent in the step (A).

4. The process for producing a sulfonyl chloride compound according to claim 1, wherein the reaction is conducted while blowing an inert gas into the reaction mixture of step (A) and step (B).

5. The process for producing a sulfonyl chloride compound according to claim 1, wherein the reaction is conducted in the absence of a solvent in the step (B).

6. The process for producing a sulfonyl chloride compound according to claim 5, wherein the chlorinating agent is a chlorinating agent having a boiling point of 90° C. or less at ordinary pressure in the step (B).

7. The process for producing a sulfonyl chloride compound according to claim 6, wherein the chlorinating agent having a boiling point of 90° C. or less at ordinary pressure is thionyl chloride in the step (B).

8. The process for producing a sulfonyl chloride compound according to claim 6, wherein the reaction temperature is from a boiling point of the chlorinating agent to 120° C. in the step (B).

9. The process for producing a sulfonyl chloride compound according to claim 1, wherein $R^1$ is a C1-C6 unsubstituted alkyl group, $R^2$ and $R^3$ are hydrogen atoms and $R^4$ is the halogen atom.

10. The process for producing a sulfonyl chloride compound according to claim 1, wherein step (C) comprises simultaneously adding the reaction mixture obtained in step (B) and the aqueous inorganic base solution into a container and mixing.

11. The process for producing a sulfonyl chloride compound according to claim 10, further comprising adding a pH buffer solution to the container prior to adding the reaction mixture and the aqueous inorganic base solution to the container.

* * * * *